United States Patent
Chen et al.

(10) Patent No.: US 11,897,848 B2
(45) Date of Patent: Feb. 13, 2024

(54) CRYSTALLINE FORMS OF OZANIMOD AND PROCESSES FOR PREPARATION THEREOF

(71) Applicant: RECEPTOS LLC, New York, NY (US)

(72) Inventors: Minhua Chen, Suzhou (CN); Yanfeng Zhang, Suzhou (CN); Xiaoting Zhai, Suzhou (CN); Kaiqiang Yan, Suzhou (CN); Chaohui Yang, Suzhou (CN); Xiaoyu Zhang, Suzhou (CN)

(73) Assignee: RECEPTOS LLC, New York, NY (US)

( * ) Notice: Subject to any disclaimer, the term of this patent is extended or adjusted under 35 U.S.C. 154(b) by 120 days.

(21) Appl. No.: 17/339,080

(22) Filed: Jun. 4, 2021

(65) Prior Publication Data

US 2021/0292287 A1 Sep. 23, 2021

Related U.S. Application Data

(62) Division of application No. 16/326,353, filed as application No. PCT/CN2017/098125 on Aug. 18, 2017, now Pat. No. 11,028,060.

(30) Foreign Application Priority Data

Aug. 19, 2016 (CN) .......................... 201610687206.5
Sep. 14, 2016 (CN) .......................... 201610822328.0

(51) Int. Cl.
| | |
|---|---|
| *C07D 271/06* | (2006.01) |
| *A61P 1/04* | (2006.01) |
| *A61P 25/00* | (2006.01) |
| *A61P 37/02* | (2006.01) |
| *A61P 1/00* | (2006.01) |
| *A61K 31/4245* | (2006.01) |

(52) U.S. Cl.
CPC ........ *C07D 271/06* (2013.01); *C07B 2200/13* (2013.01)

(58) Field of Classification Search
CPC .......... C07D 271/06; A61P 1/04; A61P 25/00; A61P 37/02; A61P 1/00; C07B 2200/13; A61K 31/4245
See application file for complete search history.

(56) References Cited

U.S. PATENT DOCUMENTS

| | | |
|---|---|---|
| 10,882,830 B2 | 1/2021 | Chen et al. |
| 11,028,060 B2 | 6/2021 | Chen et al. |
| 11,111,223 B2 | 9/2021 | Chen et al. |
| 11,117,876 B2 | 9/2021 | Chen et al. |
| 2011/0172202 A1 | 7/2011 | Martinborough et al. |
| 2019/0241530 A1* | 8/2019 | Sheng ..................... A61K 9/19 |
| 2020/0031784 A1 | 1/2020 | Sheng et al. |
| 2020/0157065 A1 | 5/2020 | Chen et al. |

FOREIGN PATENT DOCUMENTS

| | | |
|---|---|---|
| CN | 102118972 A | 7/2011 |
| CN | 102762100 A | 10/2012 |
| CN | 107840830 A | 3/2018 |
| WO | 2009/151529 A1 | 12/2009 |
| WO | 2011/060392 A1 | 5/2011 |
| WO | 2015/066515 A1 | 5/2015 |
| WO | 2016/164180 A1 | 10/2016 |
| WO | 2017/215617 A1 | 12/2017 |
| WO | 2018/049632 A1 | 3/2018 |
| WO | 2018/050091 A1 | 3/2018 |

OTHER PUBLICATIONS

Byrn et al., Pharmaceutical solids: a strategic approach to regulatory considerations. Pharm Res. 1995;12(7):945-954.
Caira, Crystalline Polymorphism of Organic Compounds. Topics in Current Chemistry. 1998;198;163-208.
Campeta et al., Development of a targeted polymorph screening approach for a complex polymorphic and highly solvating API. J Pharm Sci. Sep. 2010;99(9):3874-86.
Huan, Journal of International Pharmaceutical Research. Aug. 31, 2016;43(4):786.
Jacob et al., Solid State Crystallinity, Amorphous State, and Its Implications in the Pharmaceutical Process. IJPSR. 2011;2(3):472-482.
Jiang et al., Research and Development of Sphingosine 1-Phosphate Modulators. Progress in Pharmaceutical Sciences. Jul. 31, 2016;40(7):548-554.

(Continued)

*Primary Examiner* — Sun Jae Yoo
(74) *Attorney, Agent, or Firm* — McCarter & English, LLP; Wei Song

(57) ABSTRACT

The present disclosure relates to novel crystalline forms of ozanimod and preparation method thereof. The provided crystalline forms of ozanimod comprise crystalline form CS9, crystalline form CS10 and crystalline form CS11, and can be used for treating autoimmune diseases, particularly used for preparing drugs for treating multiple sclerosis and ulcerative colitis. The crystalline forms of the present disclosure have one or more advantages in solubility, stability, hygroscopicity and processability and provide new and better choices for the preparation of ozanimod drug product, and are very valuable for drug development.

(I)

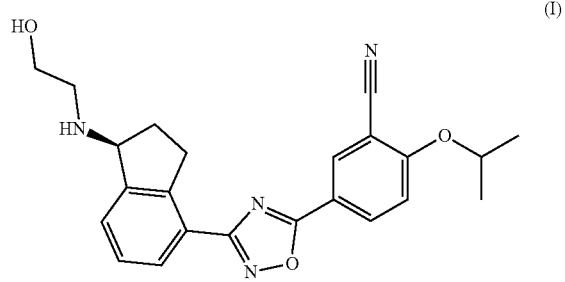

20 Claims, 12 Drawing Sheets

(56) References Cited

OTHER PUBLICATIONS

Scott et al., Ozanimod (RPC1063) is a potent sphingosine-1-phosphate receptor-1 (S1P) and receptor-5 (S1P5) agonist with autoimmune disease-modifying activity. Br J Pharmacol. 2016;173(11):1778-1792.
International Search Report and Written Opinion for Application No. PCT/CN2017/088314, dated Aug. 30, 2017, 13 pages.
International Search Report and Written Opinion for Application No. PCT/CN2018/102034, dated Nov. 29, 2018, 11 pages.

* cited by examiner

CRYSTALLINE FORMS OF OZANIMOD AND PROCESSES FOR PREPARATION THEREOF

CROSS-REFERENCE TO RELATED APPLICATIONS

This application is a Divisional Application of U.S. application Ser. No. 16/326,353, filed on Feb. 18, 2019, which is the U.S. national stage filing, under 35 U.S.C. § 371(c), of International Application No. PCT/CN2017/098125, filed on Aug. 18, 2017, which claims priority to Chinese Patent Application No. 201610822328.0, filed on Sep. 14, 2016; and Chinese Patent Application No. 201610687206.5, filed on Aug. 19, 2016.

TECHNICAL FIELD

The present disclosure relates to the field of pharmaceutical chemistry, particularly relates to crystalline forms of ozanimod and processes for preparation thereof.

BACKGROUND

Multiple sclerosis is the most common primary demyelinating disease that affects the central nervous system. Multiple sclerosis can cause a variety of symptoms, including changes in sensation, visual problems, muscle weakness, depression, difficulties with coordination and speech, severe fatigue, cognitive impairment, balance problem, body heat and pain. Serve multiple sclerosis can lead to movement disorder and disabilities. Multiple sclerosis lesions are located in the brain or spinal cord and multiple sclerosis gradually causes the plaque damage of the nerve myelin sheath of brain and spinal cord (demyelination). Myelin sheath scar can affect the signal transmission of the nerve axons, and the control over the outer periphery of the brain and the spinal cord is lost, so that stiffness or losses of function of multiple parts are happened. Globally, multiple sclerosis affects about 2.3 million people, with an average age of 20-40 years. The pathogenesis of multiple sclerosis is not clear. Multiple sclerosis is considered as an autoimmune disease, and an effective radical treatment method is not available at present.

Sphingosine-1-phosphate family members participate in numerous important cell physiological processes, such as cell proliferation, angiogenesis, immune cell trafficking, etc. The sphingosine-1-phosphate receptors (S1PR) are a class of G protein-coupled receptors, which can regulate a variety of downstream signaling molecules and cellular functions and have already been considered as a novel relative target molecule used for regulating various diseases (such as multiple sclerosis, lung cancer, psoriasis, kidney injury, uremia and pain.). Fingolimod is the first S1PR protein modulator and the first oral regulatory drug for multiple sclerosis, which was approved by the FDA in the United States in 2010.

Ozanimod is a novel, oral, selective modulator of S1PR developed by Receptos for the treatment of autoimmune diseases, especially for the treatment of multiple sclerosis and ulcerative colitis having a significant effect. In clinical trials, ozanimod's clinical results showed better safety data than fingolimod, especially when it comes to heart safety. Ozanimod has very excellent pharmacokinetics, efficacy and safety data in clinical trials, which can perfectly meet the differentiated development strategy and is expected to be the best second-generation S1PR modulator drug. The chemical structure of the drug is shown as formula (I) and it is an S-enantiomer.

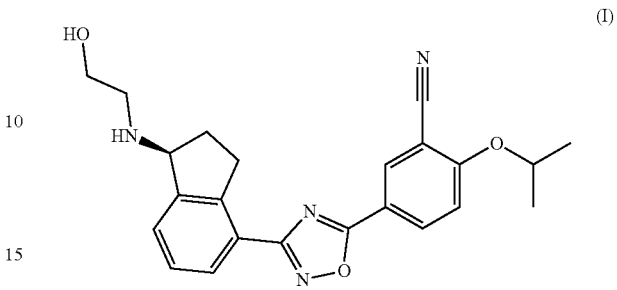

(I)

Different crystalline forms of the same solid chemical drug are significantly different in solubility, stability, fluidity, compressibility and the like, which can in turn affect the safety and efficacy of the drug products (refer to K. Knapman, Modern Drug Discovery, 3, 53-54, 57, 2000.) and leads to differences in clinical efficacy. CN102762100A disclosed the compound of formula (I) and the preparation method of the R-enantiomer of ozanimod, while there is no solid form or crystalline form of ozanimod disclosed in the prior art. The prior art has neither guidance nor inspiration for finding the crystalline forms. Therefore, it is necessary to perform comprehensive polymorph screening of ozanimod to select a crystalline form which is the most suitable for drug development.

The inventors of the present disclosure have found three crystalline forms of ozanimod through research studies, which provides new choices for the preparation of ozanimod drug product.

SUMMARY

The present disclosure provides novel crystalline forms of ozanimod, and processes for preparation and use thereof.

According to the objective of the present disclosure, crystalline form CS9 of ozanimod is provided (hereinafter referred to as Form CS9). Said Form CS9 is a hydrate.

The X-ray powder diffraction pattern of Form CS9 shows characteristic peaks at 2theta values of $11.5°±0.2°$ $4.3°±0.2°$ and $24.4°±0.2°$ using CuKα radiation.

Furthermore, the X-ray powder diffraction pattern of Form CS9 shows one or two or three diffraction peaks at 2theta values of $10.5°±0.2°$, $25.9°±0.2°$ and $16.6°±0.2°$. Preferably, the X-ray powder diffraction pattern of Form CS9 shows diffraction peaks at 2theta values of $10.5°±0.2°$, $25.9°±0.2°$ and $16.6°±0.2°$.

Furthermore, the X-ray powder diffraction pattern of Form CS9 shows one or two or three characteristic peaks at 2theta values of $11.0°±0.2°$, $18.8°±0.2°$ and $23.2°±0.2°$. Preferably, the X-ray powder diffraction pattern of Form CS9 shows diffraction peaks at 2theta values of $11.0°±0.2°$, $18.8°±0.2°$ and $23.2°±0.2°$.

In a preferred embodiment, the X-ray powder diffraction pattern of Form CS9 shows characteristic peaks at 2theta values of $11.5°±0.2°$, $4.3°±0.2°$, $24.4°±0.2°$, $10.5°±0.2°$, $25.9°±0.2°$, $16.6°±0.2°$, $11.0°±0.2°$, $18.8°±0.2°$ and $23.2°±0.2°$.

Without any limitation being implied, in a preferred embodiment, the X-ray powder diffraction pattern of Form CS9 is substantially as depicted in FIG. 1.

According to the objective of the present disclosure, the present disclosure further provides the process for preparing Form CS9. The process comprises:

Suspending ozanimod into a mixture of solvents selected from cyclic ethers and arenes, heating to dissolve the solid. Adding polymer into the clear solution and then crash cooled at low temperature to obtain white solid. The solid is confirmed to be Form CS9 of ozanimod.

Said mixture of solvents selected from cyclic ethers and arenes is preferably 1, 4-dioxane and toluene, and the volume ratio of 1, 4-dioxane and toluene is preferably 1:1.

Said heating temperature is preferably 40° C. to 80° C., more preferably 50° C.

Said cooling temperature is preferably −20° C. to 4° C., more preferably −20° C.

According to the objective of the present disclosure, crystalline form CS10 of ozanimod is provided (hereinafter referred to as Form CS10). Said Form CS10 is an anhydrate.

The X-ray powder diffraction pattern of Form CS10 shows characteristic peaks at 2theta values of 5.7°±0.2°, 25.0°±0.2° and 26.6°±0.2° using CuKα radiation.

Furthermore, the X-ray powder diffraction pattern of Form CS10 shows one or two or three diffraction peaks at 2theta values of 13.4°±0.2°, 28.3°±0.2° and 16.2°±0.2°. Preferably, the X-ray powder diffraction pattern of Form CS10 shows diffraction peaks at 2theta values of 13.4°±0.2°, 28.3°±0.2° and 16.2°±0.2°.

Furthermore, the X-ray powder diffraction pattern of Form CS10 shows one or two or three characteristic peaks at 2theta values of 8.6°±0.2°, 19.3°±0.2° and 14.6°±0.2°. Preferably, the X-ray powder diffraction pattern of Form CS10 shows three diffraction peaks at 2theta values of 8.6°±0.2°, 19.3°±0.2° and 14.6°±0.2°.

In a preferred embodiment, the X-ray powder diffraction pattern of Form CS10 shows characteristic peaks at 2theta values of 5.7°±0.2°, 25.0°±0.2°, 26.6°±0.2°, 13.4°±0.2°, 28.3°±0.2°, 16.2°±0.2°, 8.6°±0.2°, 19.3°±0.2° and 14.6°±0.2°.

Without any limitation being implied, in a preferred embodiment, the X-ray powder diffraction pattern of Form CS10 is substantially as depicted in FIG. 5.

According to the objective of the present disclosure, the present disclosure further provides the process for preparing Form CS10. The process comprises:

Suspending amorphous ozanimod into a mixture of acetone and water, stirring at room temperature to obtain solid. The obtained solid is Form CS10 of ozanimod.

Said volume ratio of acetone and water is 1:10 to 5:1, preferably 1:1.

Process for preparing said amorphous ozanimod comprises: heating the solid of ozanimod at 150° C. to make solid fused, and then crash cooling at −20° C. to obtain amorphous. The X-ray powder diffraction pattern is substantially as depicted in FIG. 4.

According to the objective of the present disclosure, crystalline form CS11 of ozanimod is provided (hereinafter referred to as Form CS11). Said Form CS11 is an anhydrate.

The X-ray powder diffraction pattern of Form CS11 shows characteristic peaks at 2theta values of 5.7°±0.2°, 24.6°±0.2° and 25.3°±0.2° using CuKα radiation.

Furthermore, the X-ray powder diffraction pattern of Form CS11 shows one or two or three diffraction peaks at 2theta values of 13.4°±0.2°, 13.9°±0.2° and 27.0°±0.2°. Preferably, the X-ray powder diffraction pattern of Form CS11 shows diffraction peaks at 2theta values of 13.4°±0.2°, 13.9°±0.2° and 27.0°±0.2°.

Furthermore, the X-ray powder diffraction pattern of Form CS11 shows one or two or three or four characteristic peaks at 2theta values of 16.2°±0.2°, 23.3°±0.2°, 26.1°±0.2° and 8.6°±0.2°. Preferably, the X-ray powder diffraction pattern of Form CS11 shows diffraction peaks at 2theta values of 16.2°±0.2°, 23.3°±0.2°, 26.1°±0.2° and 8.6°±0.2°.

In a preferred embodiment, the X-ray powder diffraction pattern of Form CS11 shows characteristic peaks at 2theta values of 5.7°±0.2°, 24.6°±0.2°, 25.3°±0.2°, 13.4°±0.2°, 13.9°±0.2°, 27.0°±0.2°, 16.2°±0.2°, 23.3°±0.2°, 26.1°±0.2° and 8.6°±0.2°.

Without any limitation being implied, in a preferred embodiment, the X-ray powder diffraction pattern of Form CS11 is substantially as depicted in FIG. 8.

According to the objective of the present disclosure, the present disclosure further provides the process for preparing Form CS11. The process comprises:

Suspending amorphous ozanimod into a mixture of solvents comprising two kinds of alcohols, or a mixture of solvents selected from ketones and alkanes or halohydrocarbons and esters, and then stirring, isolating at room temperature to obtain solid. The obtained solid is Form CS11 of ozanimod.

Said mixture of solvents includes methanol and isopropanol, acetone and n-heptane, chloroform and isopropyl acetate.

Preferably, said volume ratio of methanol and isopropanol is 1:3, volume ratio of acetone and n-heptane is 1:1 and volume ratio of chloroform and isopropyl acetate is 1:2.

Process for preparing said amorphous of ozanimod comprises: Heating the solid of ozanimod at 150° C. to make solid fused, and then crash cooling at −20° C. to obtain amorphous. The X-ray powder diffraction pattern is substantially as depicted in FIG. 4.

Another objective of the present disclosure is to provide a pharmaceutical composition comprising a therapeutically effective amount of ozanimod Form CS9 or Form CS10 or Form 11 or combinations thereof and pharmaceutically acceptable carriers, diluents or excipients.

Ozanimod Form CS9, Form CS10 or Form CS11 or combinations thereof provided by present disclosure can be used for preparing drugs of selective modulator of sphingosine-1-phosphate receptor.

Ozanimod Form CS9, Form CS10 or Form CS11 or combinations thereof provided by present disclosure can be used for preparing drugs for treating ulcerative colitis.

Ozanimod Form CS9, Form CS10 or Form CS11 or combinations thereof provided by present disclosure can be used for preparing drugs for treating multiple sclerosis.

Said "room temperature" in the present disclosure is not an exact temperature value and refers to 10-30° C.

Said "stirring" is accomplished by using a conventional method in the field such as a magnetic stirring or a mechanical stirring and the stirring speed is 50 to 1800 r/min, preferably is 300 to 900 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished at room temperature or a higher temperature. The drying temperature is from room temperature to about 60° C., or to 40° C., or to 50° C. The drying time can be 2 to 48 hours, or overnight. Drying is accomplished in a fume hood, oven or vacuum oven.

Said "evaporating" is accomplished by using a conventional method in the field. For example, slow evaporation is to seal the container with a sealing film and puncture holes for evaporation. Rapid evaporation is to place the container open for evaporation.

Said "polymer" is a mixture of equal masses of polycaprolactone, polyoxyethylene, polymethyl methacrylate, sodium alginate, and hydroxyethyl cellulose.

The beneficial effects of the present disclosure are as follows:

At present, no patent or literature has disclosed the crystalline form of ozanimod and inventors of the present disclosure broke through this difficult problem and found several novel crystalline forms of ozanimod suitable for drug development.

The crystalline form with low hygroscopicity doesn't require special drying conditions during the preparation process, which simplifies the preparation and post-treatment process of the drug and is easy for industrial production. Form CS10 and CS11 of the present disclosure have only a small weight gain at 80% relativity humidity (RH), which is slightly hygroscopic and is beneficial for long-term storage of drugs. The crystalline form with low hygroscopicity doesn't require special storage conditions, which reduces the cost of storage and quality control, and has strong economic value.

Solubility is one of the key characteristics of a drug, which directly affects in vivo absorption of the drug. Different crystalline forms have remarkable different solubility, and will affect in vivo absorption, thus lead to differences in bioavailability. As a result, clinical safety and efficacy will be affected. Form CS9 has good solubility in water, which is beneficial to improve the bioavailability of drugs.

Stability plays an important role in judging whether a crystalline form has development value. Especially during the commercial shelf life, maintaining stable can reduce the change of drug dissolution rate and bioavailability due to crystal transformation, which is of great significance to ensure the efficacy and safety of the drug and prevent the occurrence of adverse drug reactions. Form CS10 and Form CS11 of the present disclosure are placed under the condition of 25° C./60% RH and/or 40° C./75% RH for a period of time, the crystalline form of Form CS10 and Form CS11 are not changed. This shows that Form CS10 and Form CS11 have good stability.

The crystalline forms provided by the present disclosure have advantages in solubility, hygroscopicity, stability, etc. Form CS9, Form CS10 and Form CS11 of the present disclosure have uniform particle size distribution and good dispersion, which is helpful to simplify the post-process for preparation and provides a new and better choice for the preparation of drugs containing ozanimod and is of great significance for drug development.

DETAILED DESCRIPTION OF THE DISCLOSURE

Figure 1:
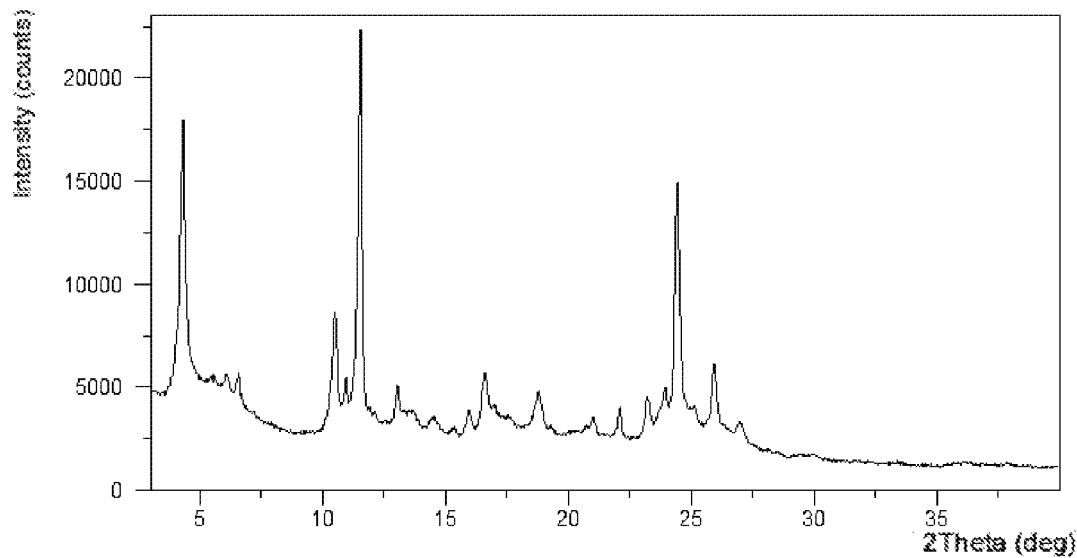
FIG. 1 shows an XRPD pattern of Form CS9 obtained in Example 1.

The present disclosure is further illustrated by the following examples in detail, but is not intended to limit the scope of the present disclosure. The skilled in the art can make improvements to the process of preparation and the instruments used within the scope of the claims, and those improvements should be considered as falling into the scope of the present disclosure. Therefore, the protective scope of the present disclosure patent should be defined by the claims.

In the following examples, the test method is generally implemented according to a conventional condition or a condition recommended by manufacturer.

The abbreviations used in the disclosure are explained as follows:

XRPD: X-ray Powder Diffraction
DSC: Differential Scanning calorimetry
TGA: Thermal Gravimetric Analysis
DVS: Dynamic Vapor Sorption
PSD: Particle Size Distribution
PLM: Polarized Light microscopy X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the differential scanning calorimetry (DSC) method of the present disclosure were as follow:

Heating rate: 10° C./min
Purge gas: nitrogen

Thermal gravimetric analysis (TGA) data in the present disclosure were acquired by a TA Q5000. The parameters of the thermal gravimetric analysis (TGA) method of the present disclosure were as follow:

Heating rate: 10° C./min
Purge gas: nitrogen

Dynamic Vapor Sorption (DVS) is measured via an SMS (Surface Measurement Systems Ltd.) intrinsic DVS. Typical Parameters for DVS test are as follows:

Temperature: 25° C.
Gas and flow rate: $N_2$, 200 mL/min
dm/dt: 0.002%/min
RH range: 0% RH to 95% RH The particle size distribution test in the present disclosure is acquired by the S3500 laser particle size analyzer of Microtrac. Microtrac S3500 is equipped with the SDC (Sample Delivery Controller). The test is carried out by wet process, and the dispersion medium is Isopar G The parameters are as follow:

| | |
|---|---|
| Size distribution: Volume | Run Time: 10 s |
| Dispersion medium: Isopar G | Particle coordinates: Standard |
| Run Number: Average of 3 runs | Fluid refractive index: 1.42 |
| Particle Transparency: Trans | Residuals: Enabled |
| Particle refractive index: 1.5 | Flow rate: 60%* |
| Particle shape: Irregular | Filtration: Enabled |
| Ultrasonication power: 30 W | Ultrasonication time: 30 s |

*Flow rate 60% is 60% of 65 mL/s.

Raw materials of ozanimod and/or a salt thereof used in the following examples are prepared by methods disclosed in CN102762100A.

Example 1

Preparation of Form CS9 of Ozanimod:

About 90 mg of ozanimod was weighed into a 20-mL glass vial, followed by adding 2 mL of 1, 4-Dioxane/toluene (1:1, v/v). The suspension was dissolved at 50° C. and filtered to obtain a clear solution. 0.2 mg of polymer was added and then the solution was crash cooled at −20° C. to obtain white solid.

Figure 2:
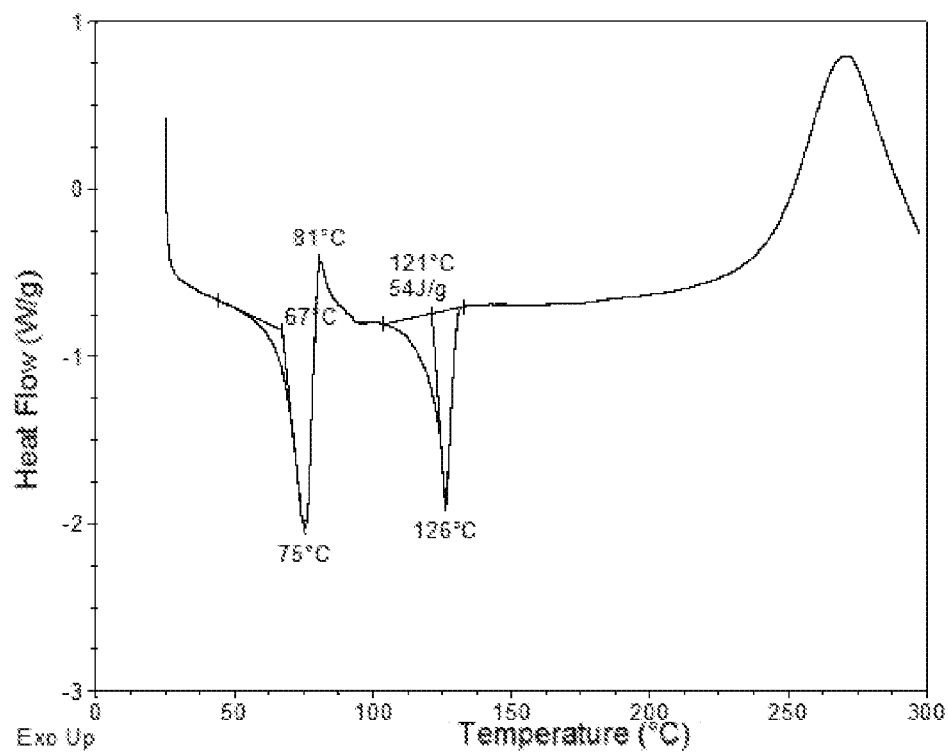
FIG. 2 shows a DSC curve of Form CS9 obtained in Example 1.
Figure 3:
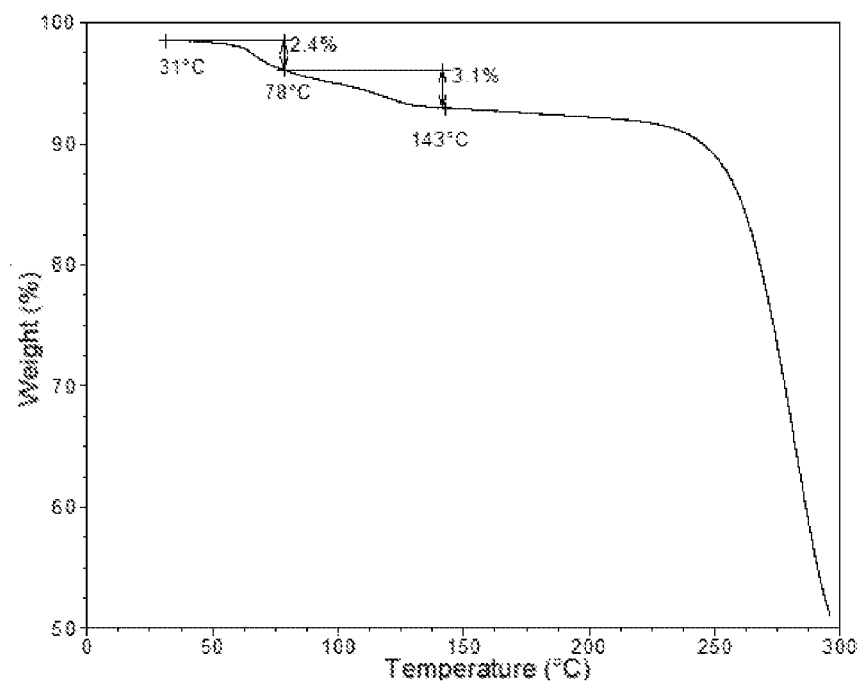
FIG. 3 shows a TGA curve of Form CS9 obtained in Example 1.

The obtained solid was confirmed to be Form CS9. The XRPD data of the solid obtained in this example are listed in Table 1. The XRPD pattern is substantially as depicted in FIG. 1. The DSC curve shows the first endothermic peak when heated to around 67° C., shows an exothermic peak when heated to around 81° C. and shows the second endothermic peak when heated to around 121° C., which is substantially as depicted in FIG. 2. The TGA curve of Form CS9 shows about 5.5% weight loss when heated to 143° C., which is substantially as depicted in FIG. 3.

TABLE 1

| 2theta | d spacing | Relative intensity % |
|---|---|---|
| 4.32 | 20.46 | 68.98 |
| 5.56 | 15.91 | 7.57 |
| 6.09 | 14.51 | 9.38 |

TABLE 1-continued

| 2theta | d spacing | Relative intensity % |
|---|---|---|
| 6.59 | 13.41 | 9.86 |
| 10.51 | 8.42 | 30.46 |
| 10.97 | 8.08 | 14.58 |
| 11.54 | 7.67 | 100.00 |
| 12.13 | 7.30 | 6.16 |
| 13.05 | 6.79 | 13.08 |
| 13.72 | 6.45 | 6.64 |
| 14.51 | 6.10 | 5.44 |
| 15.35 | 5.77 | 3.22 |
| 15.95 | 5.56 | 7.98 |
| 16.60 | 5.34 | 17.36 |
| 18.80 | 4.72 | 13.56 |
| 21.00 | 4.23 | 7.63 |
| 22.09 | 4.02 | 10.14 |
| 23.22 | 3.83 | 13.24 |
| 23.93 | 3.72 | 15.49 |
| 24.42 | 3.65 | 67.48 |
| 25.13 | 3.54 | 11.80 |
| 25.93 | 3.44 | 22.52 |
| 26.97 | 3.31 | 8.33 |
| 29.76 | 3.00 | 0.90 |
| 33.34 | 2.69 | 0.35 |
| 36.20 | 2.48 | 1.07 |
| 37.83 | 2.38 | 0.88 |

Example 2

Figure 4:
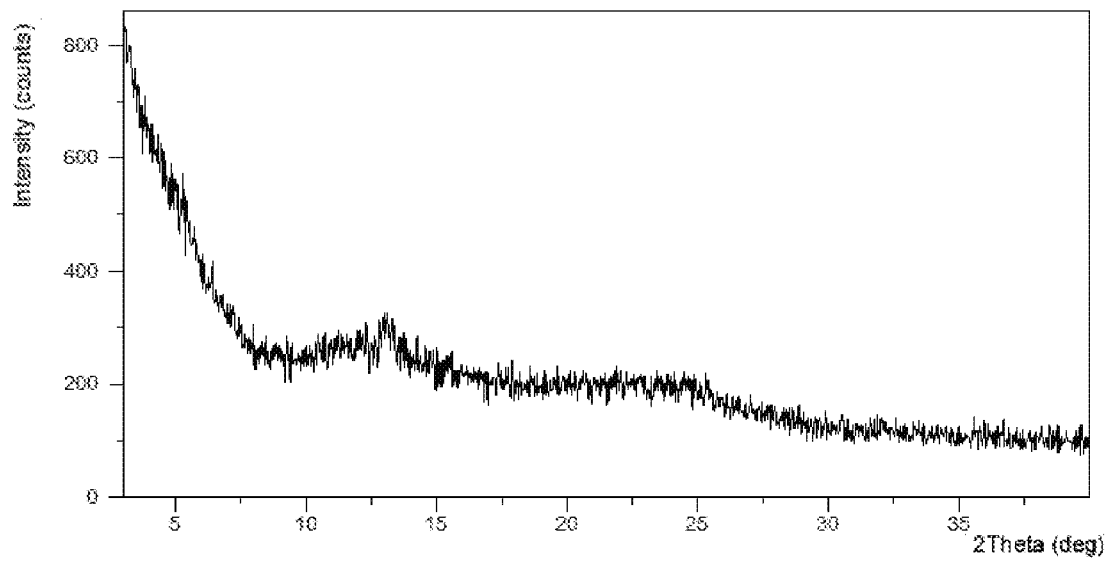
FIG. 4 shows an XRPD pattern of amorphous obtained in Example 2.

Preparation of Amorphous Ozanimod:

About 100 mg of ozanimod was weighed into a 20-mL glass vial. The glass vial was placed on 150° C. hot stage to melt the solid. And then the sample was crash cooled at −20° C. to obtain amorphous. The XRPD pattern is substantially as depicted in FIG. 4.

Example 3

Preparation of Form CS10 of Ozanimod:

About 10 mg of amorphous ozanimod was weighed into a 1.5-mL glass vial, followed by adding 0.3 mL of toluene. The suspension was stirred at room temperature to obtain solid.

Figure 5:
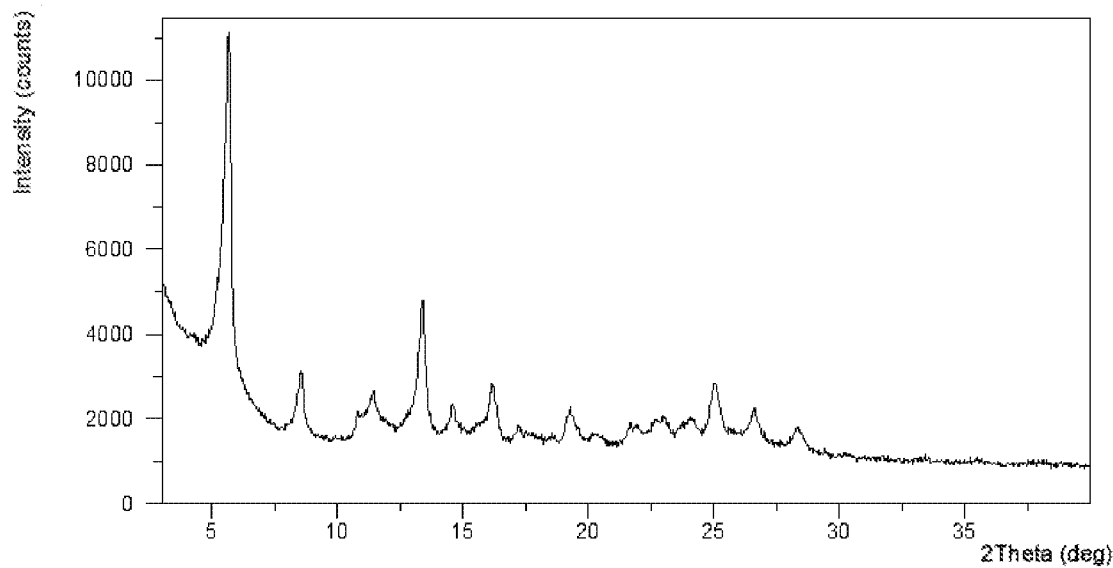
FIG. 5 shows an XRPD pattern of Form CS10 obtained in Example 3.
Figure 6:
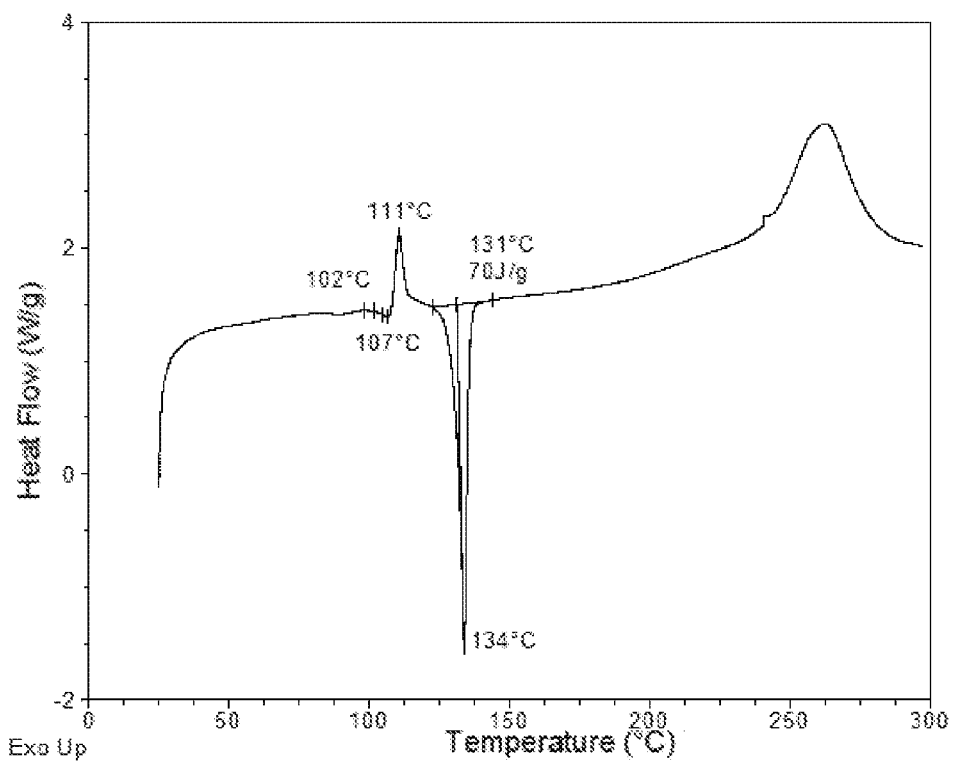
FIG. 6 shows a DSC curve of Form CS10 obtained in Example 3.
Figure 7:
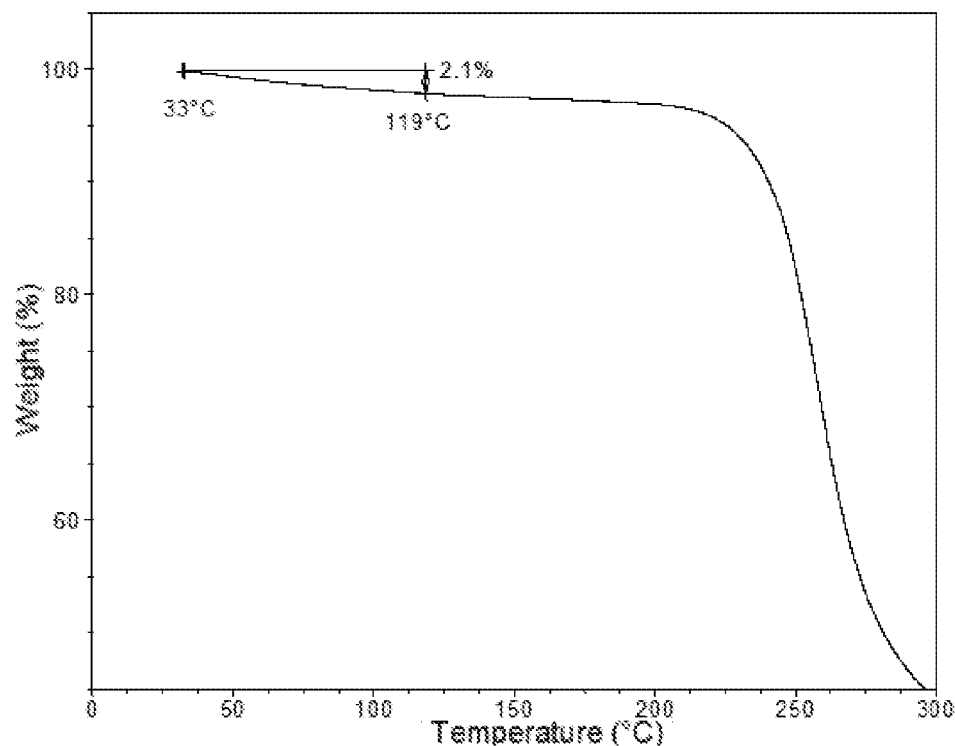
FIG. 7 shows a TGA curve of Form CS10 obtained in Example 3.

The obtained solid was confirmed to be Form CS10. The XRPD data of the solid obtained in this example are listed in Table 2. The XRPD pattern is substantially as depicted in FIG. 5. The DSC curve shows the first endothermic peak when heated to around 102° C., shows an exothermic peak when heated to around 111° C. and shows the second endothermic peak when heated to around 131° C., which is substantially as depicted in FIG. 6. The TGA curve of Form CS10 shows about 2.1% weight loss when heated to 119° C., which is substantially as depicted in FIG. 7.

TABLE 2

| 2theta | d spacing | Relative intensity % |
|---|---|---|
| 5.69 | 15.52 | 100.00 |
| 8.58 | 10.31 | 17.17 |
| 10.80 | 8.19 | 7.94 |
| 11.44 | 7.73 | 14.73 |
| 13.38 | 6.62 | 41.67 |
| 14.59 | 6.07 | 11.42 |
| 16.19 | 5.47 | 17.24 |
| 17.20 | 5.16 | 5.89 |
| 18.55 | 4.78 | 3.08 |
| 19.27 | 4.61 | 11.66 |
| 20.37 | 4.36 | 3.90 |

TABLE 2-continued

| 2theta | d spacing | Relative intensity % |
|---|---|---|
| 21.69 | 4.10 | 7.91 |
| 22.64 | 3.93 | 9.10 |
| 23.04 | 3.86 | 9.88 |
| 24.16 | 3.68 | 9.57 |
| 25.04 | 3.56 | 20.40 |
| 26.62 | 3.35 | 13.35 |
| 28.34 | 3.15 | 8.17 |
| 29.96 | 2.98 | 1.36 |
| 30.35 | 2.95 | 1.24 |
| 33.24 | 2.70 | 0.60 |
| 35.52 | 2.53 | 0.86 |
| 37.88 | 2.37 | 0.73 |

Example 4

Preparation of Form CS10 of Ozanimod:

About 10 mg of amorphous ozanimod was weighed into a 1.5-mL glass vial, followed by adding 0.3 mL of acetone/water (1:1, v/v). The suspension was stirred at room temperature to obtain a solid.

Figure 8:
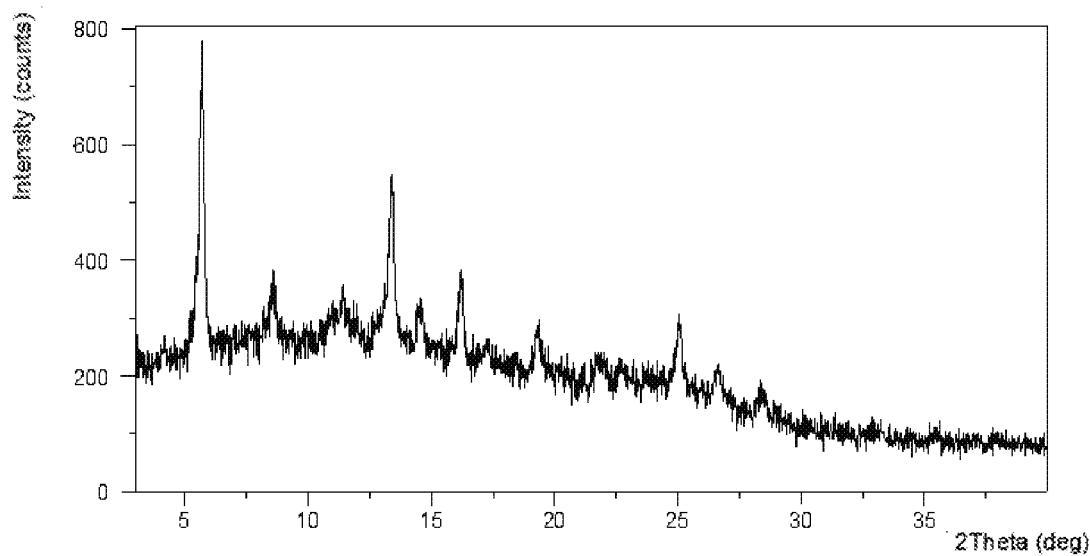
FIG. 8 shows an XRPD pattern of Form CS10 obtained in Example 4.

The obtained solid was confirmed to be Form CS10. The XRPD data of the solid prepared in this example are listed in Table 3. The XRPD pattern is substantially as depicted in FIG. 8.

TABLE 3

| 2theta | d spacing | Relative intensity % |
|---|---|---|
| 4.19 | 21.11 | 7.45 |
| 5.68 | 15.55 | 100.00 |
| 8.58 | 10.31 | 29.07 |
| 10.91 | 8.11 | 19.01 |
| 11.43 | 7.74 | 19.44 |
| 13.36 | 6.63 | 56.86 |
| 14.62 | 6.06 | 16.70 |
| 16.22 | 5.47 | 25.10 |
| 19.26 | 4.61 | 13.82 |
| 20.24 | 4.39 | 4.54 |
| 21.11 | 4.21 | 3.92 |
| 21.88 | 4.06 | 7.23 |
| 22.67 | 3.92 | 8.87 |
| 25.07 | 3.55 | 28.56 |
| 26.61 | 3.35 | 14.49 |
| 28.44 | 3.14 | 11.91 |
| 28.92 | 3.09 | 5.09 |
| 30.47 | 2.93 | 2.98 |
| 31.84 | 2.81 | 4.57 |
| 32.35 | 2.77 | 3.17 |
| 33.26 | 2.69 | 4.12 |
| 35.28 | 2.54 | 2.46 |
| 35.62 | 2.52 | 6.17 |
| 36.96 | 2.43 | 2.34 |
| 37.87 | 2.38 | 2.93 |
| 38.35 | 2.35 | 3.15 |

Example 5

Preparation of Form CS11 of Ozanimod:

About 10 mg of amorphous ozanimod was weighed into a 1.5-mL glass vial, followed by adding 0.3 mL of methanol/isopropanol (1:3, v/v). The suspension was stirred at room temperature to obtain a solid.

Figure 9:
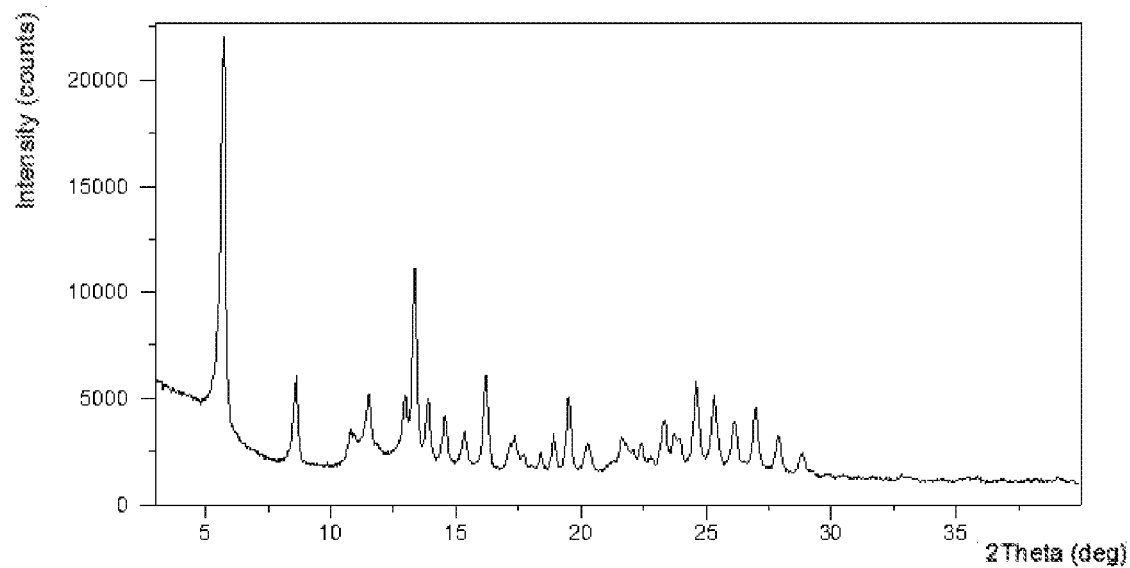
FIG. 9 shows an XRPD pattern of Form CS11 obtained in Example 5.
Figure 10:
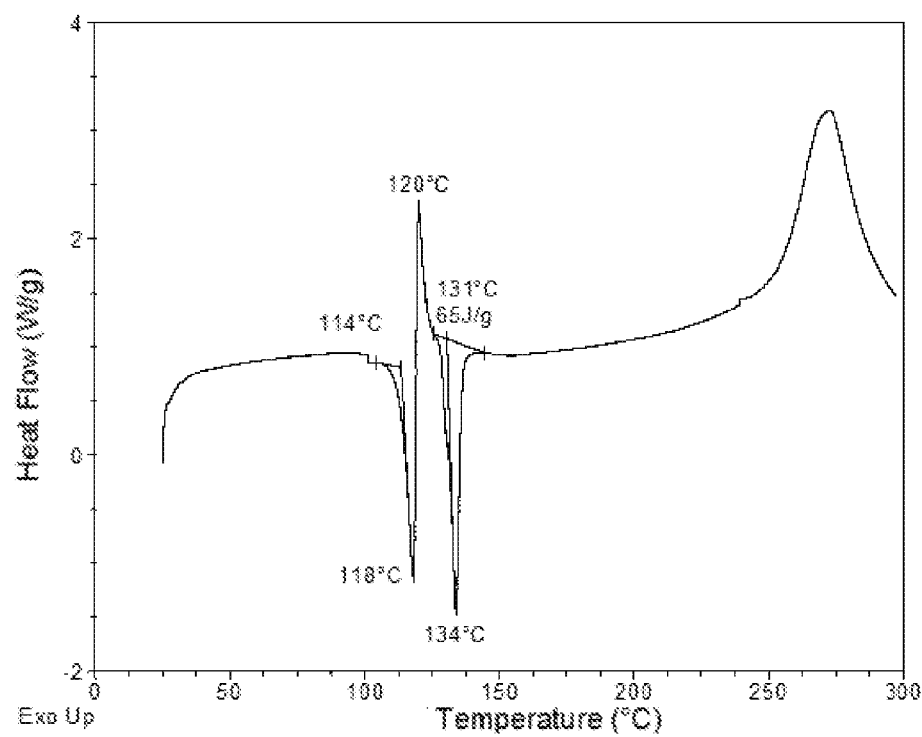
FIG. 10 shows a DSC curve of Form CS11 obtained in Example 5.
Figure 11:
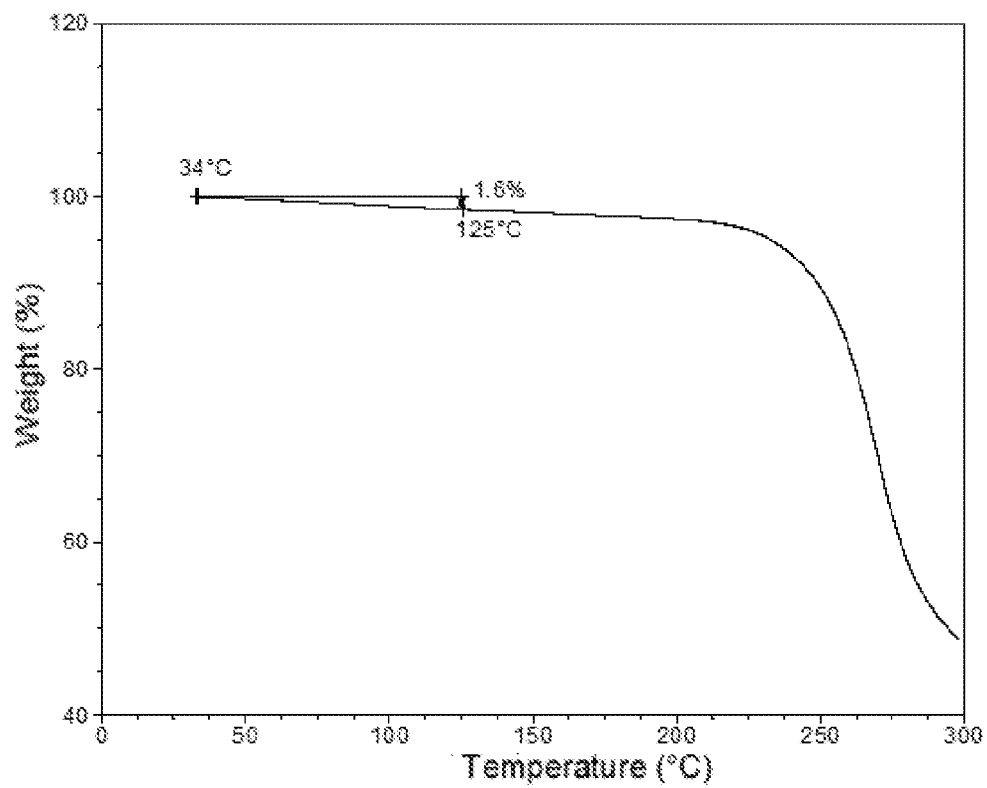
FIG. 11 shows a TGA curve of Form CS11 obtained in Example 5.

The obtained solid was confirmed to be Form CS11. The XRPD data of the solid obtained in this example are listed in Table 4. The XRPD pattern is displayed in FIG. 9. The DSC curve shows the first endothermic peak when heated to around 114° C., shows an exothermic peak when heated to around 120° C. and shows the second endothermic peak when heated to around 131° C., which is substantially as depicted in FIG. 10. The TGA curve of Form CS11 shows about 1.6% weight loss when heated to 125° C., which is substantially as depicted in FIG. 11.

TABLE 4

| 2theta | d spacing | Relative intensity % |
|---|---|---|
| 5.73 | 15.42 | 100.00 |
| 8.63 | 10.25 | 21.96 |
| 10.77 | 8.22 | 8.71 |
| 11.53 | 7.68 | 18.55 |
| 12.97 | 6.83 | 18.49 |
| 13.36 | 6.63 | 52.38 |
| 13.90 | 6.37 | 17.48 |
| 14.57 | 6.08 | 13.78 |
| 15.35 | 5.77 | 9.55 |
| 16.21 | 5.47 | 24.67 |
| 17.36 | 5.11 | 8.45 |
| 17.71 | 5.01 | 3.98 |
| 18.40 | 4.82 | 4.56 |
| 18.89 | 4.70 | 8.43 |
| 19.51 | 4.55 | 19.05 |
| 20.24 | 4.39 | 7.02 |
| 21.63 | 4.11 | 9.17 |
| 22.42 | 3.97 | 7.39 |
| 23.33 | 3.81 | 13.96 |
| 23.71 | 3.75 | 9.97 |
| 23.95 | 3.72 | 9.18 |
| 24.58 | 3.62 | 23.17 |
| 25.32 | 3.52 | 20.14 |
| 26.13 | 3.41 | 13.52 |
| 26.96 | 3.31 | 17.28 |
| 27.89 | 3.20 | 10.30 |
| 28.82 | 3.10 | 5.82 |
| 32.86 | 2.73 | 0.91 |
| 35.58 | 2.52 | 0.80 |
| 39.10 | 2.30 | 1.02 |

Example 6

Preparation of Form CS11 of Ozanimod:

About 10 mg of amorphous ozanimod was weighed into a 1.5-mL glass vial, followed by adding 0.3 mL of acetone/n-heptane (1:1, v/v). The suspension was stirred at room temperature to obtain a solid.

Figure 12:
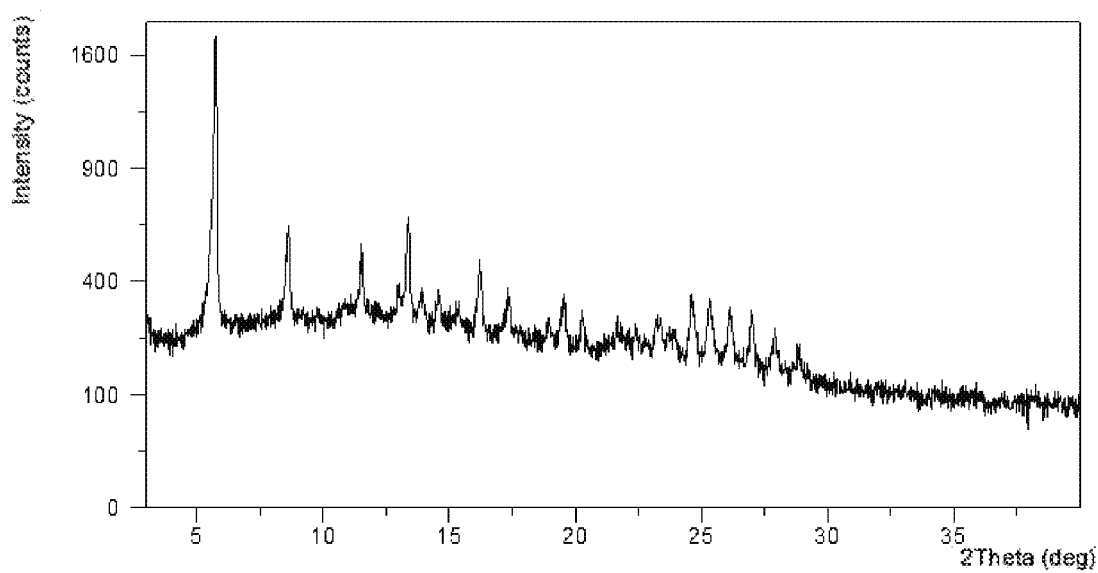
FIG. 12 shows an XRPD pattern of Form CS11 obtained in Example 6.

The obtained solid was confirmed to be Form CS11. The XRPD data of the solid obtained in this example are listed in Table 5. The XRPD pattern is substantially as depicted in FIG. 12.

TABLE 5

| 2theta | d spacing | Relative intensity % |
|---|---|---|
| 5.73 | 15.41 | 100.00 |
| 6.27 | 14.10 | 5.92 |
| 8.62 | 10.25 | 30.22 |
| 11.52 | 7.68 | 21.04 |
| 13.38 | 6.62 | 32.38 |
| 13.90 | 6.37 | 12.68 |
| 14.62 | 6.06 | 9.58 |
| 15.38 | 5.76 | 8.32 |
| 16.22 | 5.46 | 20.01 |
| 17.35 | 5.11 | 14.39 |
| 18.16 | 4.88 | 6.99 |
| 18.96 | 4.68 | 6.40 |
| 19.56 | 4.54 | 12.7 |
| 20.29 | 4.38 | 9.50 |
| 21.65 | 4.11 | 8.80 |

TABLE 5-continued

| 2theta | d spacing | Relative intensity % |
|---|---|---|
| 22.42 | 3.97 | 6.96 |
| 23.28 | 3.82 | 7.57 |
| 23.91 | 3.72 | 6.54 |
| 24.27 | 3.67 | 5.72 |
| 24.62 | 3.62 | 14.80 |
| 25.35 | 3.51 | 12.85 |
| 26.15 | 3.41 | 11.22 |
| 26.93 | 3.31 | 11.32 |
| 27.04 | 3.30 | 11.40 |
| 27.90 | 3.20 | 8.34 |
| 28.79 | 3.10 | 4.18 |
| 31.56 | 2.84 | 1.50 |
| 33.45 | 2.68 | 0.67 |
| 35.54 | 2.53 | 1.11 |

Example 7

Preparation of Form CS11 of Ozanimod:

About 10 mg of amorphous ozanimod was weighed into a 1.5-mL glass vial, followed by adding 0.3 mL of chloroform/isopropyl acetate (1:2, v/v). The suspension was stirred at room temperature to obtain a solid.

Figure 13:
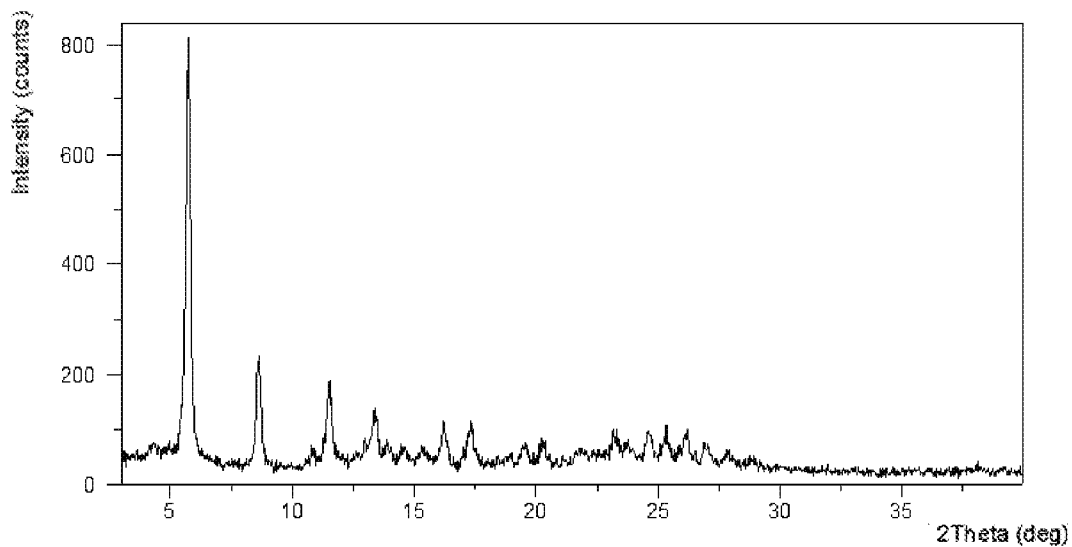
FIG. 13 shows an XRPD pattern of Form CS11 obtained in Example 7.

The obtained solid was confirmed to be Form CS11. The XRPD data of the solid prepared in this example are listed in Table 6. The XRPD pattern is substantially as depicted in FIG. 13.

TABLE 6

| 2theta | d spacing | Relative intensity % |
|---|---|---|
| 5.72 | 15.45 | 100.00 |
| 7.07 | 12.51 | 4.25 |
| 8.64 | 10.24 | 29.86 |
| 9.63 | 9.19 | 3.30 |
| 10.32 | 8.57 | 4.49 |
| 10.85 | 8.15 | 5.86 |
| 11.51 | 7.69 | 21.62 |
| 11.95 | 7.41 | 5.90 |
| 12.94 | 6.84 | 7.29 |
| 13.49 | 6.57 | 15.05 |
| 13.83 | 6.40 | 8.21 |
| 14.66 | 6.04 | 7.67 |
| 15.32 | 5.78 | 8.30 |
| 16.22 | 5.46 | 12.81 |
| 17.37 | 5.11 | 11.05 |
| 17.98 | 4.93 | 4.40 |
| 18.42 | 4.82 | 6.11 |
| 19.05 | 4.66 | 5.57 |
| 19.63 | 4.52 | 6.69 |
| 20.26 | 4.38 | 7.50 |
| 21.14 | 4.20 | 4.90 |
| 21.59 | 4.12 | 6.04 |
| 22.39 | 3.97 | 6.30 |
| 23.14 | 3.84 | 10.97 |
| 23.80 | 3.74 | 9.88 |
| 24.55 | 3.63 | 10.24 |
| 25.34 | 3.51 | 12.79 |
| 26.11 | 3.41 | 8.84 |
| 26.87 | 3.32 | 6.97 |
| 27.84 | 3.20 | 5.46 |
| 28.82 | 3.10 | 3.79 |
| 29.86 | 2.99 | 4.30 |
| 33.29 | 2.69 | 3.75 |
| 34.14 | 2.63 | 4.44 |

Example 8

Figure 14:
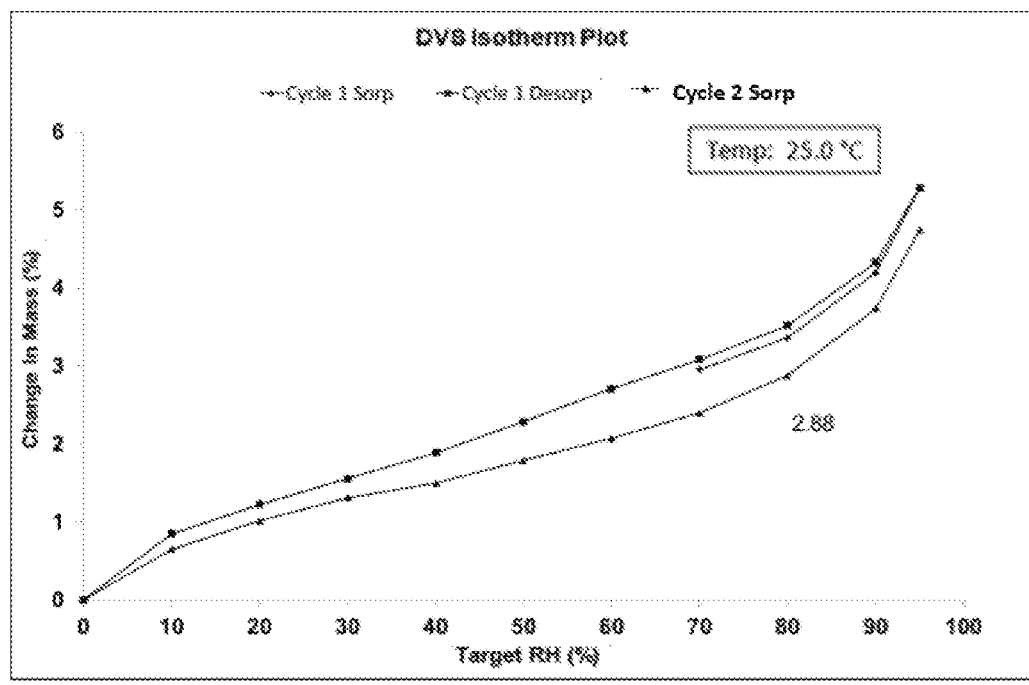
FIG. 14 shows a DVS plot of Form CS9 in Example 8.

Hygroscopicity Assessment of Form CS9 of Ozanimod:
Dynamic vapor sorption (DVS) was applied to test hygroscopicity of Form CS9 with about 10 mg of samples. The result is listed in Table 7. The DVS plot was substantially as depicted in FIG. 14.

TABLE 7

| Crystal Form | Weight Gain under 80% RH |
|---|---|
| Form CS9 | 2.88% |

The results indicates that the weight gain of Form CS9 under 80% RH is 2.88%. According to the criteria of hygroscopicity, Form CS9 is hygroscopic.

Example 9

Figure 15:
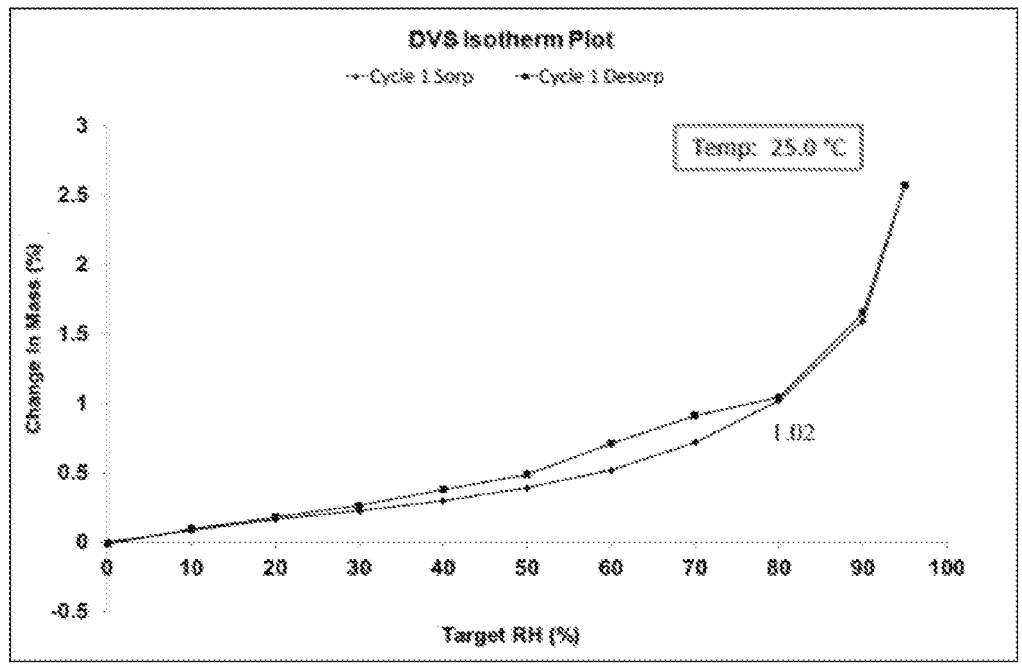
FIG. 15 shows a DVS plot of Form CS10 in Example 9.

Hygroscopicity Assessment of Form CS10 of Ozanimod:
Dynamic vapor sorption (DVS) was applied to test hygroscopicity of Form CS10 with about 10 mg of samples. The result is listed in Table 8. The DVS plot is substantially as depicted in FIG. 15.

TABLE 8

| Crystal Form | Weight Gain under 80% RH |
|---|---|
| Form CS10 | 1.02% |

The result indicates that the weight gain of Form CS10 under 80% RH is 1.02%. According to the criteria of hygroscopicity, Form CS10 is slightly hygroscopic.

Example 10

Figure 16:
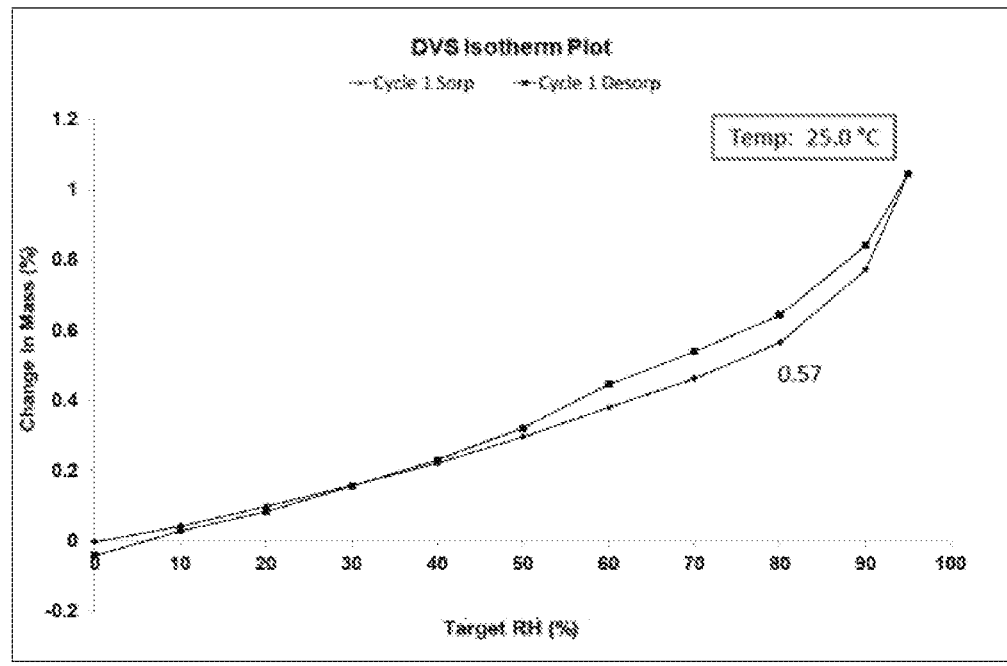
FIG. 16 shows a DVS plot of Form CS11 in Example 10.

Hygroscopicity Assessment of Form CS11 of Ozanimod:
Dynamic vapor sorption (DVS) was applied to test hygroscopicity of Form CS11 with about 10 mg of samples. The result is listed in Table 9. The DVS plot is substantially as depicted in FIG. 16.

TABLE 9

| Crystal Form | Weight Gain under 80% RH |
|---|---|
| Form CS11 | 0.57% |

The result indicates that the weight gain of Form CS11 under 80% RH is 0.57%. According to the criteria of hygroscopicity, Form CS11 is slightly hygroscopic.

Example 11

Solubility Assessment of Form CS9 of Ozanimod:
Form CS9 of ozanimod was suspended into $H_2O$ to obtain saturated solution. After being equilibrated for 1 h, 4 h and 24 h, concentrations of the saturated solutions were measured by HPLC. The results are listed in Table 10.

TABLE 10

| Time (h) | Solubility in $H_2O$ (mg/mL) |
|---|---|
| 1 | 0.47 |
| 4 | 0.36 |
| 24 | 0.32 |

The result indicates that Form CS9 has good solubility in water.

Example 12

Particle Size Distribution and Morphology Study:

Certain amount of samples of Form CS9, Form CS10 and Form CS11 of ozanimod were taken for particle size distribution test. The results are shown in Table 11.

TABLE 11

| Crystal Form | MV (μm) | SD | D10 (μm) | D50 (μm) | D90 (μm) |
|---|---|---|---|---|---|
| Form CS9 | 339.9 | 267.1 | 50.97 | 284.3 | 728.7 |
| Form CS10 | 317.2 | 228.7 | 65.87 | 254.8 | 669.0 |
| Form CS11 | 137.7 | 104.4 | 27.13 | 110.4 | 286.6 |

The abbreviations used in the invention are explained as follows:
- Mv: Average particle size calculated by volume.
- D10: particle size which accounts for 10% of the particle size distribution (volume distribution).
- D50: particle size which accounts for 50% of the particle size distribution (volume distribution), also known as the median diameter.
- D90: particle size which accounts for 90% of the particle size distribution (volume distribution).

Figure 17:
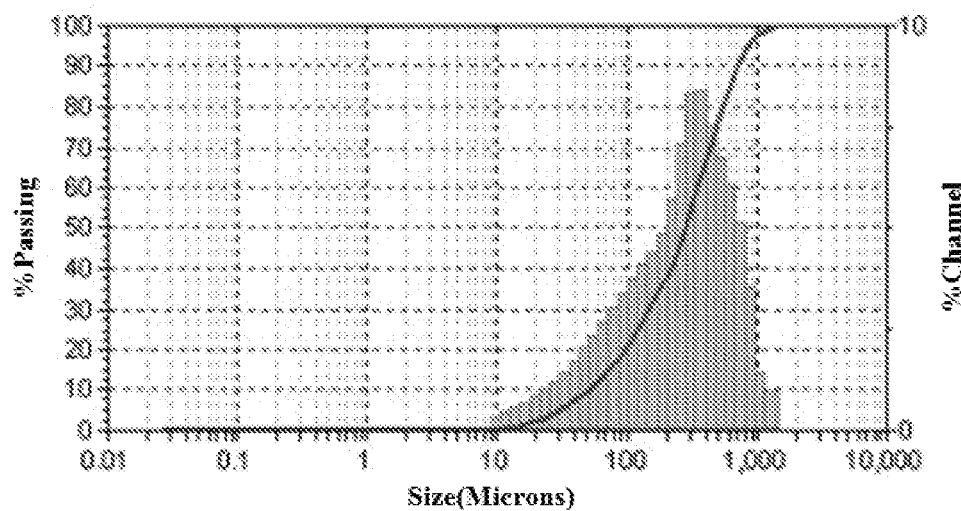
FIG. 17 shows a PSD diagram of Form CS9 in Example 12.
Figure 18:
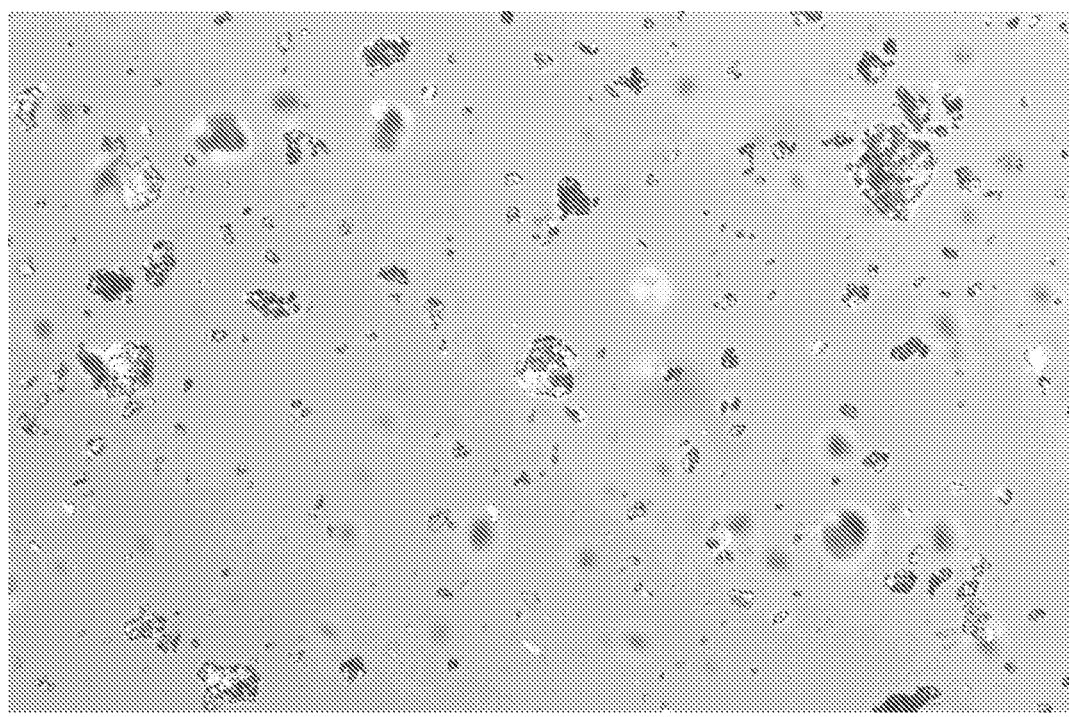
FIG. 18 shows a PLM image of Form CS9 in Example 12.

The particle size distribution (PSD) diagram and PLM image of Form CS9 were substantially as depicted in FIG. 17 and FIG. 18. The result shows that the average particle size of Form CS9 is 339.9 μm, and the particle size distribution is narrow, which presents an almost normal and uniform distribution. Furthermore, the PLM image shows that Form CS9 is small particles with good dispersion.

Figure 19:
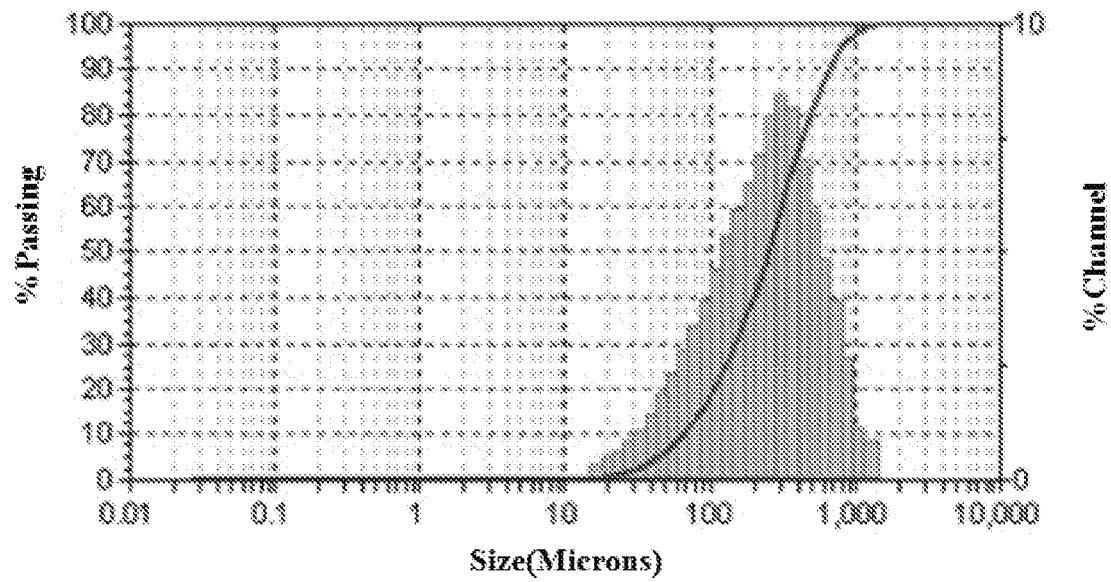
FIG. 19 shows a PSD diagram of Form CS10 in Example 12.
Figure 20:
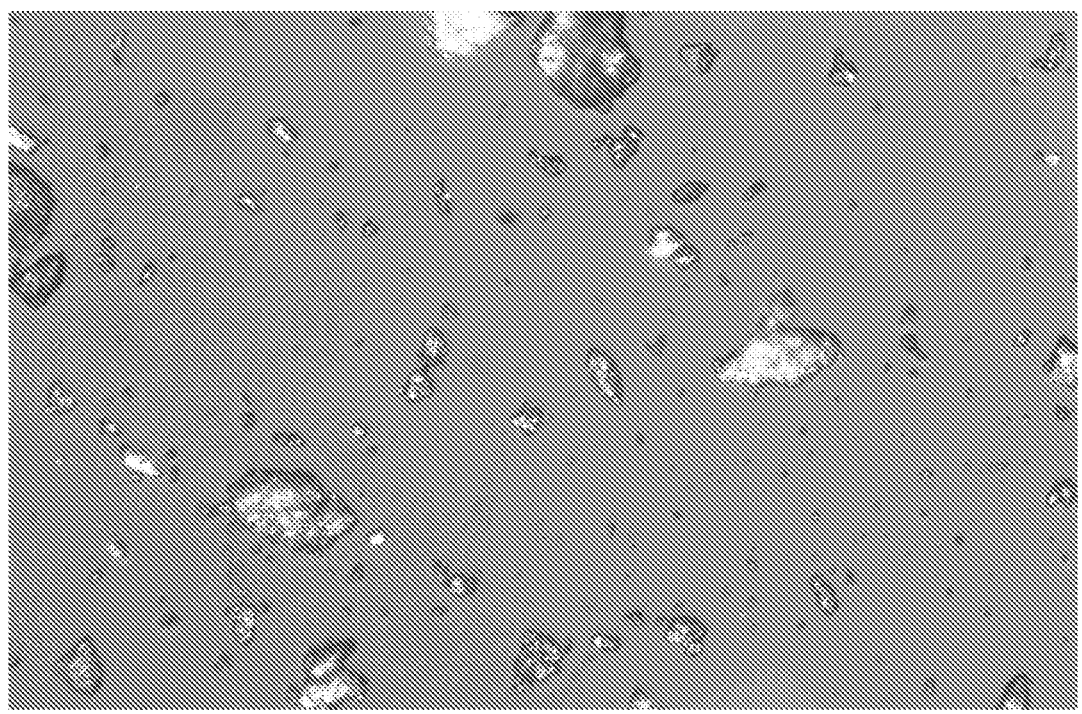
FIG. 20 shows a PLM image of Form CS10 in Example 12.

The particle size distribution (PSD) diagram and PLM plot of Form CS10 were substantially as depicted in FIG. 19 and FIG. 20. The result shows that the average particle size of Form CS10 is 317.2 μm, and the particle size distribution is narrow, which presents an almost normal and uniform distribution. Furthermore, the PLM plot shows that Form CS10 is small particles with good dispersion.

Figure 21:
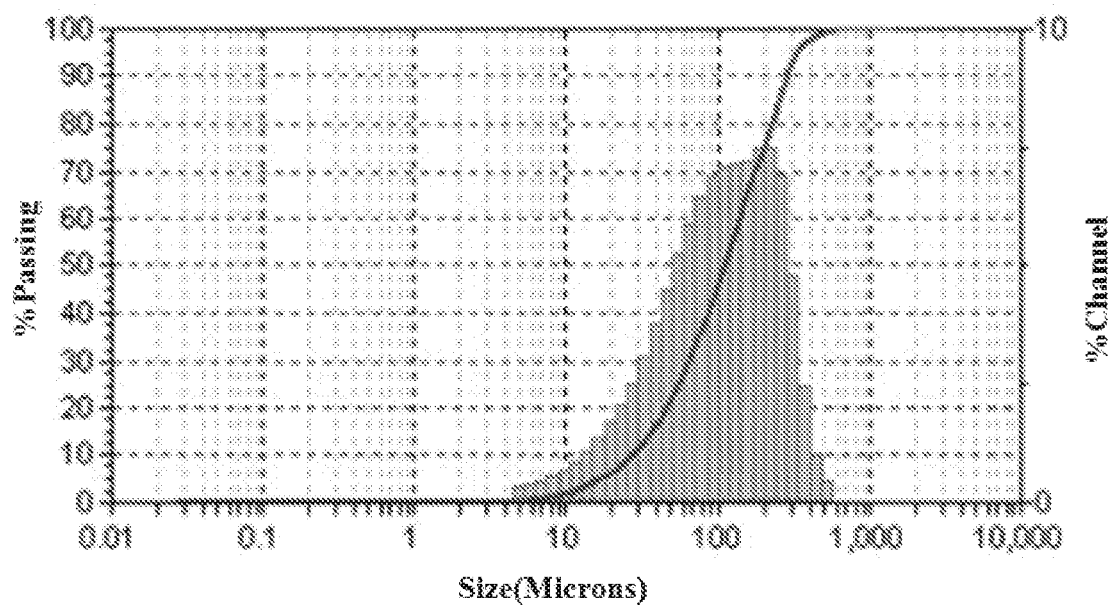
FIG. 21 shows a PSD diagram of Form CS11 in Example 12.
Figure 22:
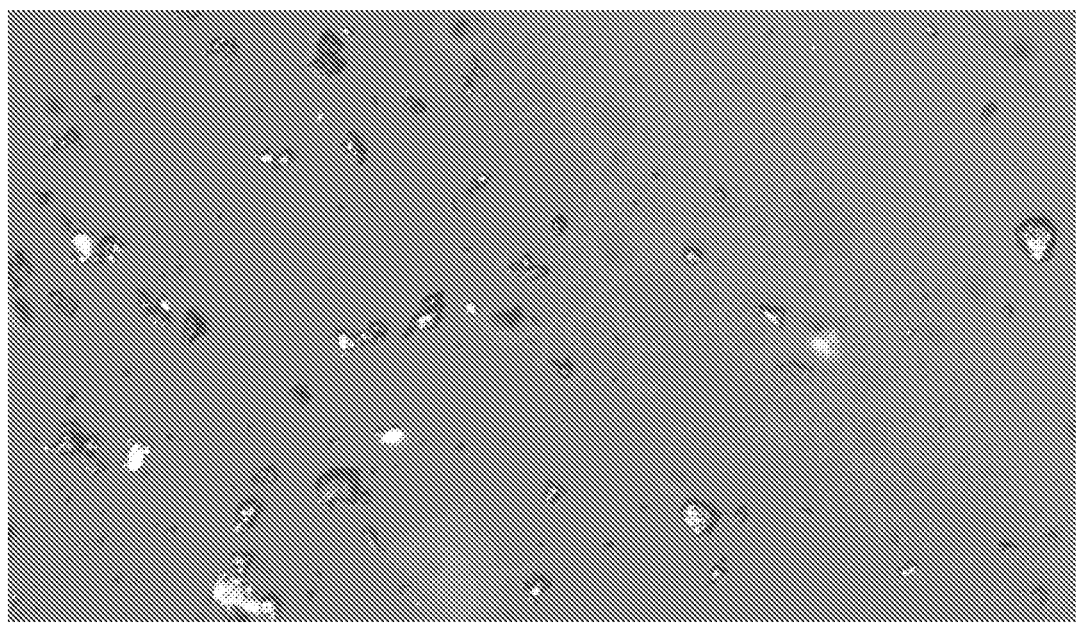
FIG. 22 shows a PLM image of Form CS11 in Example 12.

The particle size distribution (PSD) diagram and PLM plot of Form CS11 were substantially as depicted in FIG. 21 and FIG. 22. The result shows that the average particle size of Form CS11 is 137.7 μm, and the particle size distribution is narrow, which presents an almost normal and uniform distribution. Furthermore, the PLM plot shows that Form CS11 is small particles with good dispersion.

Example 13

Figure 23:
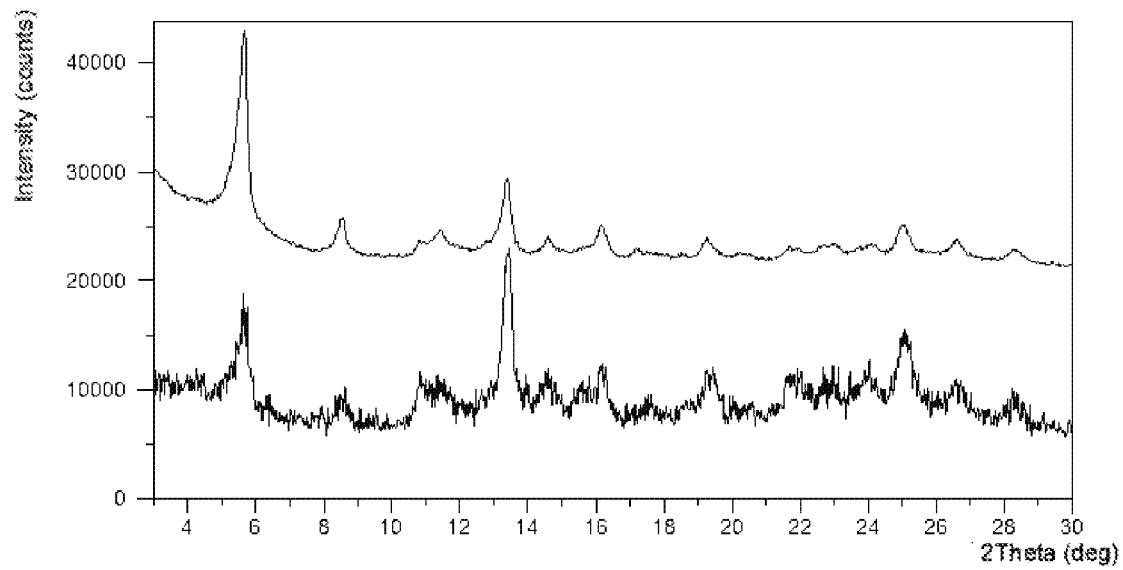
FIG. 23 shows an XRPD pattern overlay of Form CS10 before and after stability assessment in Example 13.

Stability Assessment of Form CS10 of Ozanimod:

Sample of Form CS10 was placed in chamber with controlled temperature and relative humidity at 40° C./75% RH for 2 weeks, and then the solids were sampled for XRPD test. The XRPD pattern overlay was substantially as depicted in FIG. 23 (from top to bottom: XRPD pattern of ozanimod Form CS10 before and after being stored under 40° C./75% RH for 2 weeks). No form change was observed for Form CS10 after being stored at 40° C./75% RH for 2 weeks. It can be seen that Form CS10 of ozanimod has good stability.

Example 14

Figure 24:
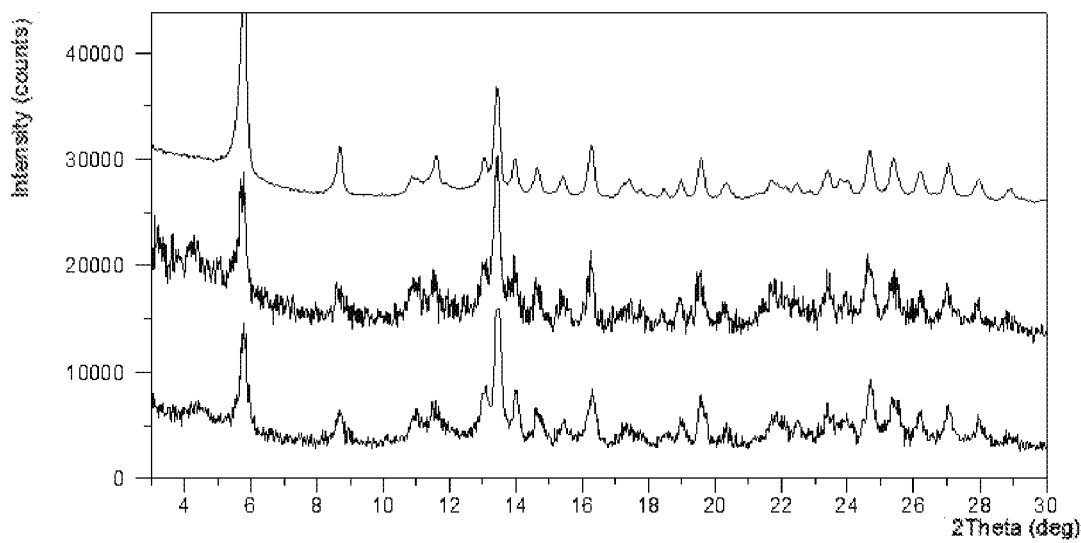
FIG. 24 shows an XRPD pattern overlay of Form CS11 before and after stability assessment in Example 14.

Stability Assessment of Form CS11 of Ozanimod:

Two samples of Form CS11 of ozanimod were placed in chamber with controlled temperature and relative humidity at 25° C./60% RH and 40° C./75% RH for 2 weeks. XRPD and HPLC were used to test the crystalline form and chemical purity. The XRPD overlay pattern was substantially as depicted in FIG. 24 (from top to bottom: XRPD pattern of ozanimod Form CS11 before and after being stored under 25° C./60% RH and 40° C./75% RH for 2 weeks).

No form change and obvious purity decrease were observed for Form CS11 after being stored at 25° C./60% RH and 40° C./75% RH for 2 weeks. It can be seen that Form CS11 has good stability.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure

What is claimed is:

1. A crystalline form CS11 of ozanimod, wherein the X-ray powder diffraction pattern shows characteristic peaks at 2theta values of 5.7°±0.2°, 24.6°±0.2° and 0.3°±0.2°.

2. The crystalline form CS11 of ozanimod according to claim 1, wherein the X-ray powder diffraction pattern shows one or two or three characteristic peaks at 2theta values of 13.4°±0.2°, 13.9°±0.2° and 27.0°±0.2°.

3. The crystalline form CS11 of ozanimod according to claim 1, wherein the X-ray powder diffraction pattern shows one or more characteristic peaks at 2theta values of 16.2°±0.2°, 23.3°±0.2°, 26.1°±0.2° and 8.6°±0.2°.

4. A process for preparing crystalline form CS11 of ozanimod according to claim 1, wherein the process comprises:
   suspending amorphous ozanimod into a mixture of solvents comprising two kinds of alcohols, or a mixture of solvents selected from ketones and alkanes or halohydrocarbons and esters, and then
   stirring at room temperature, isolating to obtain form CS11 of ozanimod.

5. The process for preparing crystalline form CS11 of ozanimod according to claim 4, wherein said mixture of solvents is selected from methanol and isopropanol, or acetone and heptane, or chloroform and isopropyl acetate.

6. The process for preparing crystalline form CS11 of ozanimod according to claim 5, wherein volume ratio of methanol and isopropanol is 1:3, volume ratio of acetone and n-heptane is 1:1 and volume ratio of chloroform and isopropyl acetate is 1:2.

7. The process for preparing crystalline form CS11 of ozanimod according to claim 4, wherein the amorphous ozanimod was prepared by melting ozanimod solid at 150° C., and then crash cooling at −20° C. to obtain amorphous ozanimod.

8. A pharmaceutical composition, wherein said pharmaceutical composition comprises a therapeutically effective amount of crystalline form CS11 of ozanimod according to claim 1, and a pharmaceutically acceptable carrier, a diluent or an excipient.

9. A method for selective modulating sphingosine-1-phosphate receptor, comprising administering to a patient in need thereof a therapeutically effective amount of the crystalline form CS11 of ozanimod according to claim 1.

10. A method for treating ulcerative colitis, comprising administering to a patient in need thereof a therapeutically effective amount of the crystalline form CS11 of ozanimod according to claim 1.

11. A method for treating multiple sclerosis, comprising administering to a patient in need thereof a therapeutically effective amount of the crystalline form CS11 of ozanimod according to claim 1.

12. The crystalline form CS11 of ozanimod according to claim 2, wherein the X-ray powder diffraction pattern shows one or more characteristic peaks at 2theta values of 16.2°±0.2°, 23.3°±0.2°, 26.1°±0.2° and 8.6°±0.2°.

13. A pharmaceutical composition, wherein said pharmaceutical composition comprises a therapeutically effective amount of crystalline form CS11 of ozanimod according to claim 2, and a pharmaceutically acceptable carrier, a diluent or an excipient.

14. A method for selective modulating sphingosine-1-phosphate receptor, comprising administering to a patient in need thereof a therapeutically effective amount of the crystalline form CS11 of ozanimod according to claim 2.

15. A method for treating ulcerative colitis, comprising administering to a patient in need thereof a therapeutically effective amount of the crystalline form CS11 of ozanimod according to claim 2.

16. A method for treating multiple sclerosis, comprising administering to a patient in need thereof a therapeutically effective amount of the crystalline form CS11 of ozanimod according to claim 2.

17. A pharmaceutical composition, wherein said pharmaceutical composition comprises a therapeutically effective amount of crystalline form CS11 of ozanimod according to claim 12, and a pharmaceutically acceptable carrier, a diluent or an excipient.

18. A method for selective modulating sphingosine-1-phosphate receptor, comprising administering to a patient in need thereof a therapeutically effective amount of the crystalline form CS11 of ozanimod according to claim 12.

19. A method for treating ulcerative colitis, comprising administering to a patient in need thereof a therapeutically effective amount of the crystalline form CS11 of ozanimod according to claim 12.

20. A method for treating multiple sclerosis, comprising administering to a patient in need thereof a therapeutically effective amount of the crystalline form CS11 of ozanimod according to claim 12.

* * * * *

UNITED STATES PATENT AND TRADEMARK OFFICE
CERTIFICATE OF CORRECTION

| | |
|---|---|
| PATENT NO. | : 11,897,848 B2 |
| APPLICATION NO. | : 17/339080 |
| DATED | : February 13, 2024 |
| INVENTOR(S) | : Minhua Chen et al. |

Page 1 of 1

It is certified that error appears in the above-identified patent and that said Letters Patent is hereby corrected as shown below:

In the Claims

At Column 14, Claim number 1, Line number 29, replace "0.3°" with -- 25.3° --.

Signed and Sealed this
Tenth Day of September, 2024

Katherine Kelly Vidal
*Director of the United States Patent and Trademark Office*